(12) United States Patent
Elgård et al.

(10) Patent No.: US 10,034,670 B2
(45) Date of Patent: Jul. 31, 2018

(54) MEDICAL IMPLANT DETACHMENT MECHANISM AND INTRODUCER ASSEMBLY

(71) Applicant: COOK MEDICAL TECHNOLOGIES LLC, Bloomington, IN (US)

(72) Inventors: Per Elgård, Haslev (DK); Allan Torp, Bjaeverskov (DK)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 160 days.

(21) Appl. No.: 14/961,076

(22) Filed: Dec. 7, 2015

(65) Prior Publication Data

US 2016/0157869 A1  Jun. 9, 2016

(30) Foreign Application Priority Data

Dec. 8, 2014  (GB) .................................. 1421760.8

(51) Int. Cl.
*A61M 29/00* (2006.01)
*A61B 17/12* (2006.01)
*A61B 17/00* (2006.01)

(52) U.S. Cl.
CPC .... *A61B 17/12109* (2013.01); *A61B 17/1214* (2013.01); *A61B 2017/00336* (2013.01);
(Continued)

(58) Field of Classification Search
CPC ........ A61B 17/12109; A61B 17/12113; A61B 17/1214; A61B 17/12145; A61B 17/1215; A61B 17/12154
See application file for complete search history.

(56) References Cited

U.S. PATENT DOCUMENTS 3,827,437 A    8/1974  Inaba
5,133,727 A    7/1992  Bales et al.
(Continued)

FOREIGN PATENT DOCUMENTS

DE    2850156 A1    6/1980
DE    2945237       5/1981
(Continued)

OTHER PUBLICATIONS

Examination Report for GB1421760.8, dated Oct. 26, 2016.
Extended European Search Report for EP App. No. 15275237.4-1654, dated Apr. 13, 2016.

*Primary Examiner* — Gregory Anderson
*Assistant Examiner* — Sarah Simpson
(74) *Attorney, Agent, or Firm* — Brinks Gilson & Lione (57) ABSTRACT

A detachment mechanism for an introducer assembly is designed to hold a coupling element of an implantable medical device until its desired release within a patient's vessel. The detachment mechanism includes a body portion having first and second gripper arm elements which grip onto the coupling element of the medical device. The gripper arms are naturally biased into a closed position by means of resiliency of the body element. For this purpose, an actuating device or opening element is provided which includes an enlarged head which can be pulled against tapering internal surface of the body portion of the detachment mechanism in order to force the gripper arms open, thereby to release the medical device from the introducer assembly. The detachment mechanism, being naturally in the closed configuration, reliably holds a medical device to the introducer assembly until it is desired to release the latter into the patient's vessel.

12 Claims, 4 Drawing Sheets

(52) U.S. Cl.
CPC ............... *A61B 2017/00477* (2013.01); *A61B 2017/00862* (2013.01); *A61B 2017/00964* (2013.01); *A61B 2017/12054* (2013.01)

(56) References Cited

U.S. PATENT DOCUMENTS

| | | | |
|---|---|---|---|
| 5,601,600 A | 2/1997 | Ton | |
| 5,722,989 A | 3/1998 | Fitch | |
| 5,814,062 A * | 9/1998 | Sepetka | ........... A61B 17/12022 606/108 |
| 6,102,932 A | 8/2000 | Kurz | |
| 6,217,549 B1 * | 4/2001 | Selmon | ................ A61M 29/02 604/106 |
| 6,277,125 B1 | 8/2001 | Barry et al. | |
| 6,989,020 B2 | 1/2006 | Jones et al. | |
| 2007/0270930 A1 | 11/2007 | Schenck | |

FOREIGN PATENT DOCUMENTS

| | | | | |
|---|---|---|---|---|
| DE | 3407708 A1 | 9/1985 | | |
| DE | 41145136 | 11/1992 | | |
| DE | 19547617 C1 | 9/1997 | | |
| DE | 202010000786 U1 | 3/2011 | | |
| DE | 2850156 | * | 6/2017 | ........... A61B 17/221 |
| EP | 2777542 A2 | 9/2014 | | |
| WO | WO 03/073961 | * | 9/2003 | |
| WO | WO 2006/082100 | 8/2006 | | |
| WO | WO 2010/130297 | 11/2010 | | |

* cited by examiner

MEDICAL IMPLANT DETACHMENT MECHANISM AND INTRODUCER ASSEMBLY

CROSS-REFERENCE TO RELATED APPLICATIONS

This application claims the benefit of priority under 35 U.S.C. § 119(a) to Great Britain Patent Application No. GB 1421760.8, filed Dec. 8, 2014, which is hereby incorporated by reference in its entirety.

TECHNICAL FIELD

The present invention relates to a medical implant detachment mechanism and to an introducer assembly including such a detachment mechanism.

BACKGROUND ART

Implantable medical devices are in common use for treating a variety of vascular and other medical conditions. Where possible, these devices are advantageously introduced into the patient by an endoluminal procedure form a remote percutaneous entry point, such as from the femoral artery or the jugular vein. Introducer assemblies are used for this purpose, which typically include a delivery sheath or catheter through which the medical device is carried, often on a suitable device carrier. The Seldinger technique is commonly used.

It is important that the implantable medical device is securely held to the introducer assembly in order to ensure that it is properly positioned at the desired treatment site and only then released in controlled manner and at the desired time. In many instances the implantable medical device is preloaded and fixed to the carrier at the stage of assembly of the apparatus, in which case there is rarely any risk of the medical device being improperly held or releasing without intention. On the other hand, in some instances the medical device is chosen in situ, that is in the course of a medical procedure, in which case it is up to the medical practitioner to fit the medical device to the introducer. A typical example are embolization coils, where the medical practitioner will choose the length and/or size of coil in dependence upon the state of the vessel and degree of occlusion required as determined in the course of the medical procedure. It is common to need to fit a plurality of coils, typically of different size, during the medical procedure, until the required degree of occlusion has been achieved. There is a risk in such situations that the medical device will be improperly attached to the carrier and as a result that the device will be incorrectly deployed in the patient's vessel. This can occur in particular when a fixed size carrier or sheath is used during the procedure.

Examples of prior art medical implant delivery devices may be found in U.S. Pat. No. 5,601,600, U.S. Pat. No. 6,989,020, U.S. Pat. No. 6,277,125, U.S. Pat. No. 5,133,727, U.S. Pat. No. 3,827,437, WO-2006/082100, WO-2010/130297, DE-2,945,237, DE-2,850,156, DE-3,407,708, DE-4,115,136 and German Utility Model DE-U-20/2010,000,786.

DISCLOSURE OF THE INVENTION

The present invention seeks to provide an improved medical implant detachment mechanism and an improved introducer assembly.

According to an aspect of the present invention, there is provided a medical implant detachment mechanism for holding and releasing a medical implant in an introducer assembly, the detachment mechanism having a longitudinal axis, a proximal end and a distal end, and including: a jaw unit including a plurality of jaw elements located at the distal end of the device, the jaw elements having a closed configuration and an open configuration and being configured to be in the closed configuration when unbiased, the jaw elements forming a medical implant coupling chamber designed to receive a coupling element of a medical implant, the jaw unit including an enclosure separate from the coupling chamber and disposed proximally of the coupling chamber; a jaw opening element disposed in the enclosure of the jaw unit, the jaw opening element having a first, non-biasing, position maintaining the jaw elements in the closed configuration and being longitudinally movable from the first position to a second position, wherein in the second position the jaw opening element biases the jaw elements from the closed configuration to the open configuration; wherein the jaw opening element includes a head member disposed within the enclosure and the jaw unit of the enclosure including at least one rounded or tapering inner wall against which the head member is able to press when longitudinally moved to bias the jaw elements into the open configuration.

The detachment mechanism provides a mechanism by which a medical device can be gripped by means solely of the closing bias of the jaw elements, with the result that once the device, specifically a coupling element of the device, has been fitted into the jaw elements, it is reliably held thereby until a positive action is effected to actuate the jaw release element. This contrasts with some prior art detachment mechanisms which are biased to a release configuration and held closed only by a secondary element, often the delivery sheath. With such prior art structures it is possible that the medical device becomes detached form the carrier as it is fed into the carrier sheath, leading to the problems indicated above.

Furthermore, having a chamber for the jaw opening element which is separate from the coupling chamber ensures that the jaw opening element can remain away from the coupling element of the medical implant, thereby reducing the risk that the jaw opening element will interfere with, hamper or hinder the release of the medical implant from the coupling chamber. It will be appreciated that the term "separate" is used in the functional or operational sense. In the embodiment described below, a passage exists between the enclosure and chamber but this does not affect the fact that the opening element and the implant coupling element are retained in their respective enclosure and chamber, that is separated from one another.

In the preferred embodiment, the second position of the jaw opening element is proximal of the first position, and the jaw opening element is retracted proximally in the longitudinal direction to open the jaw elements. In practice, as described below, the assembly provides for the clinician to pull back an actuator element, which releases the medical device in a secure and controlled operation. Furthermore, the jaw opening element is in this configuration moved away from the coupling element in order to release the medical device, thereby avoiding any risk of hampering or hindering its release.

Advantageously, the jaw opening element includes an enlarged head disposed within the enclosure, the head being optionally rounded or spherical.

There may be provided an end-stop adjacent the jaw elements, preferably disposed in the enclosure, and which in practice limits forward or distal movement of the jaw opening element towards the chamber where the implant coupling element is held.

Preferably, there is provided a trigger wire having a proximal end and a distal end, the distal end of the trigger wire being attached to the jaw opening element and the proximal end of the trigger wire being actuatable to retract the jaw opening element proximally in the longitudinal direction from the first position to the second position.

The jaw elements advantageously have facing concave inner surfaces, which may be partially spherical.

In the preferred embodiment, the device includes two jaw elements, disposed substantially opposite one another. It is not excluded, though, that there may be provided more than two jaw elements, for instance three, four or more.

Advantageously, the detachment mechanism is formed from a cannula, the jaw elements being cut from the cannula.

According to another aspect of the present invention, there is provided an introducer assembly including:

a medical implant detachment mechanism having a longitudinal axis, a proximal end and a distal end, and including a jaw unit including a plurality of jaw elements located at the distal end of the device, the jaw elements having a closed configuration and an open configuration and being configured to be in the closed configuration when unbiased, the jaw elements forming a medical implant coupling chamber designed to receive a coupling element of a medical implant, the jaw unit including an enclosure separate from the coupling chamber and disposed proximally of the coupling chamber; a jaw opening element disposed in the enclosure of the jaw unit, the jaw opening element having a first, non-biasing, position maintaining the jaw elements in the closed configuration and being movable from the first position to a second position, wherein in the second position the jaw opening element biases the jaw elements from the closed configuration to the open configuration;

a catheter having a proximal end and a distal end, the distal end being coupled to the detachment mechanism;

an outer sheath within which the catheter and detachment mechanism are locatable; and an implantable medical device having a coupling element disposed within the chamber of the jaw elements of the detachment mechanism, the coupling element being held in the chamber by the closed rest position of the jaw elements.

The medical device may be an embolization coil.

Other features and advantages will become apparent form the description of the preferred embodiments.

Also described is a medical implant detachment mechanism for holding and releasing a medical implant in an introducer assembly, the detachment mechanism having a longitudinal axis, a proximal end and a distal end, and including: a jaw unit including a plurality of jaw elements located at the distal end of the device, the jaw elements having a closed configuration and an open configuration and being configured to be in the closed configuration when unbiased, the jaw elements forming a medical implant coupling chamber designed to receive a coupling element of a medical implant, the jaw unit including an enclosure separate from the coupling chamber and disposed proximally of the coupling chamber; a jaw opening element disposed in the enclosure of the jaw unit, the jaw opening element having a first, non-biasing, position maintaining the jaw elements in the closed configuration and being movable from the first position to a second position, wherein in the second position the jaw opening element biases the jaw elements from the closed configuration to the open configuration.

The enclosure may include at least one round or tapering inner wall.

The jaw opening element may include an enlarged head or head member disposed within the enclosure.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

It is to be understood that the accompanying drawings are schematic and do not show the various components in their actual scale. In many instances, the drawings show scaled-up components to assist the reader.

Figure 1:
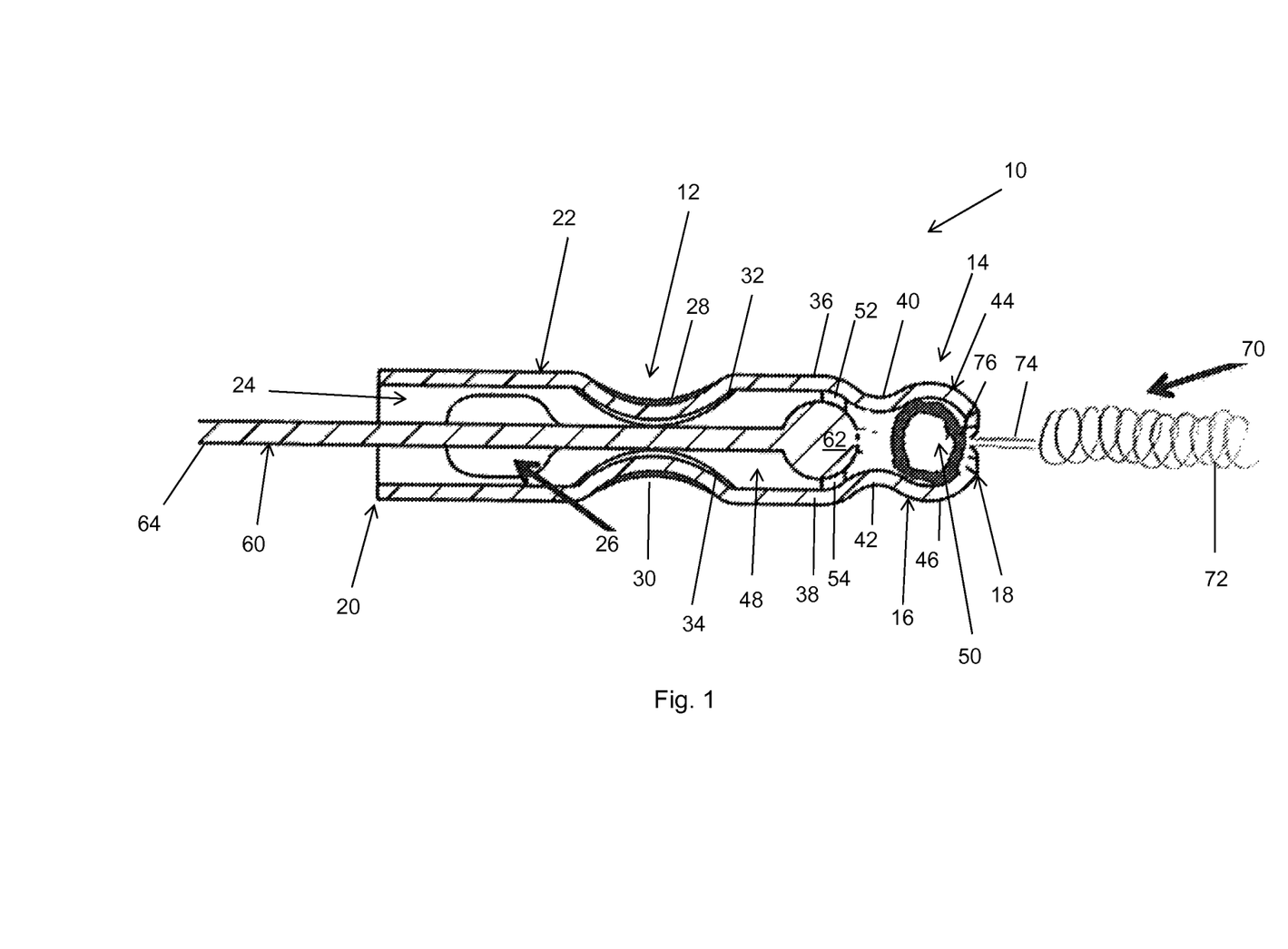
FIG. 1 is a schematic diagram in partial cross-section of an embodiment of detachment mechanism according to an embodiment of the invention.
Figure 2:
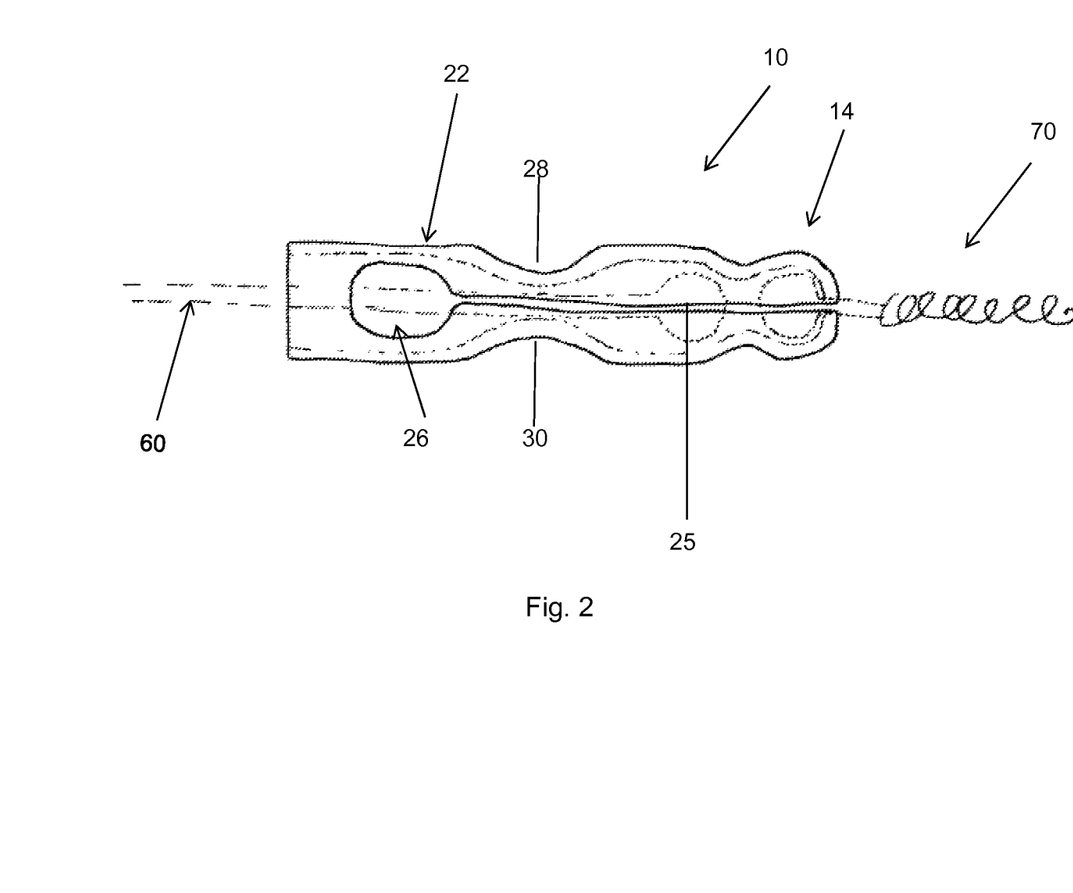
FIG. 2 is a schematic diagram of the detachment mechanism of FIG. 1.

Referring first to FIGS. 1 and 2, these show an embodiment of medical implant detachment mechanism 10 which in this example includes a body unit 12 formed as a single piece and having first and second gripping arm elements 14, 16 at one extremity 18 of the body unit 12. The extremity 18 can normally be described as a distal extremity of the detachment mechanism, being furthest from the clinician during the deployment procedure.

The body unit also includes a proximal end 20, at its other extremity.

The body unit 12 includes a first section 22 which is essentially tubular and has a lumen or chamber 24 which is open at the proximal end 20 of the body unit 12. The tubular section 22 is, in this embodiment, generally closed apart from two slits 25 which extend at opposite sides longitudinally along the body unit 12 from the extremity 18 to enlarged cut-out sections 26, of which one can be seen in each of FIGS. 1 and 2, and which act as hinge points for the device, as will become apparent below.

The body unit 12 continues from the tubular section 22 to the gripper arms 14, 16, which are integral with the tubular section 22 and disposed in opposing facing relationship to one another. The arms 14, 16 could be said to be formed by way of the slits 25. It will be appreciated that the arm elements 14, 16 may be part-tubular, thereby comprising a part of the circular or curved shape of the tubular element 22, and are preferably formed by suitably pressing the tubular element 22, as well as by cutting the tubular element 22 lengthwise from the distal end 18 to the distal end of the tubular section 22 between the two jaw elements, 14, 16 in a substantially precisely longitudinally direction.

Adjacent the distal end of the tubular section 22, each arm element 14, 16 is pinched at a pinch point 28, 30, respectively. Each pinch point is gently curved as shown in FIG.

1, so as to create gently curved internal surfaces 32, 34, respectively. The operative part of the surfaces 32, 34 are those sections which open outwardly towards the distal end 18 of the body unit 12, to act as actuation surfaces for opening the jaw elements 14, 18, as described below.

Beyond the pinch points 28, 30, the jaw units 14, 16 have straight sections 36, 38 respectively, that is being straight in the longitudinal direction of the body portion 12. The sections 36, 38 are curved in the transverse direction, mimicking the curvature of the tubular section 22. Beyond the straight sections 36, 38, each arm section 14, 16 has a distal pinch point 40, 42 and then opens outwardly to form an inwardly facing cup 44, 46 respectively. Each cup 44, 46 preferably has a part-spherical or round shape.

The straight sections 36, 38 create an actuator enclosure 48, which is generally cylindrical in form, whereas the inwardly facing jaw cups 44, 46 create a generally rounded or spherical implant chamber 50.

The distal pinch points 40, 42 act in practice to separate enclosure 48 and the chamber 50 from one another, as will apparent below. The skilled person will appreciate that separation can be achieved by a device other than a pinch point.

Disposed within the body unit 14, attached to respective arms of the arm elements 14, 16, are stop ribs or shoulders 52, 54. These are disposed at the distal end of the straight sections 36, 38 and are preferably curved in the transverse direction, most preferably rounded, and taper in closing manner towards the implant chamber 50. The stop ribs/shoulders act to stop movement in a distal direction of the actuator element, as described below.

The body unit 12 can be made of any suitable resilient material, a metal or metal alloy being preferred, examples being steel, specifically spring steel, platinum, Nitinol, palladium. These materials are relevant because they are biocompatible and to various degree radiopaque.

The detachment mechanism 10 also includes, disposed within the body unit 12, an actuator element 60, which includes an enlarged, in this embodiment spherical, actuator head 62 connected to a wire or rod 64. The wire 64 extends in the proximal direction and in practice to an external handle or manipulation unit which can be operated by a clinician. The enlarged head 62 is disposed within the chamber 48 and restricted in movement in the distal direction by the stop ribs 52, 54. The enlarged head 62 is also restricted in movement in the proximal direction by the pinch points 28, 30, specifically by the curved internal surfaces 32, 34.

As will be apparent from FIGS. 1 and 2, it is preferred that the spherical head 62 has a diameter which is notably less than the internal diameter of the body unit 12 at the straight sections 36, 38, so as to be spaced form the internal surfaces of the straight sections 38, 40.

FIGS. 1 and 2 also show an implantable medical device 70 attached to the detachment mechanism 10. Specifically, the example medical device 70 shown in FIGS. 1 and 2 is an embolization coil. The device 70 has a section of coil 72, of known form, a tie element 74, which may be part of the wire forming the coil, and a coupling element 76, which in this example is a spherical element attached to the tie element 74, again in known manner. The coupling element 76, as will be apparent from FIGS. 1 and 2, is held within the device chamber 50, and in particular within the facing cups 44, 46 of the jaw elements 14, 18. It is preferred that this is in such a manner that the gap between the jaw elements 14, 16 at the distal end 18 of the detachment mechanism 10 is large enough to accommodate the tie element 74 but sufficiently small that the cupping element 76 remains trapped within the implant chamber 50 when the jaw elements 14, 16 are closed, as in the configuration shown in FIGS. 1 and 2. It is not excluded that the coupling element 76 may be able to rotate slightly within the jaw elements 14, 18, which could assist in the deployment of the medical device 70, whilst ensuring that the medical device 70 remains firmly attached to the detachment mechanism 10 until it is decided to release the medical device 70 into the patient's oesophagus vessel.

FIGS. 1 and 2 show the detachment mechanism in its normal non-biased form, with the jaw elements 14, 16 in their normal closed configuration. In other words, the body element 12 is formed with the jaw elements 14, 16 close to one another as shown in FIG. 1, rather than being biased open. Thus, unless and until they are forced open, the jaw elements 14, 16 are in a closed configuration.

Figure 3:
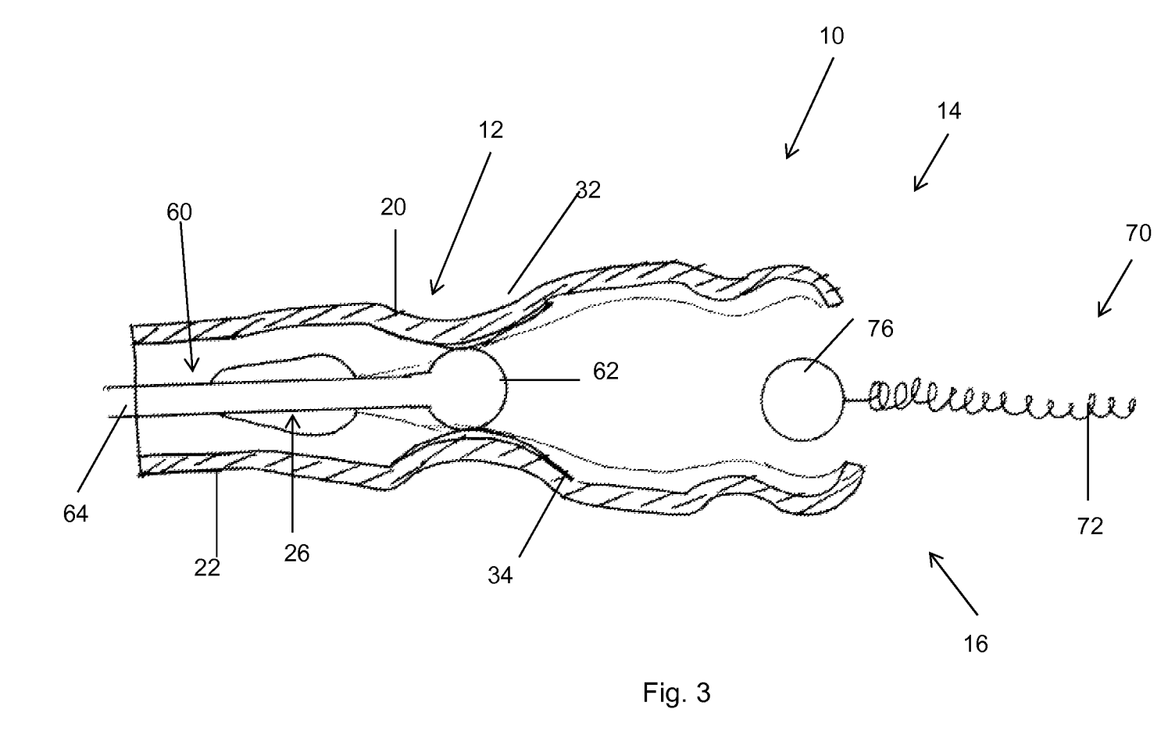
FIG. 3 is a schematic diagram of the detachment mechanism of FIGS. 1 and 2 with the jaw elements having been opened to release the medical device.

Referring now to FIG. 3, this shows the implant detachment mechanism 10 in a configuration in which the jaw elements 14, 16 have been biased to an open position, in order to release the medical implant from the detachment mechanism and, in practice, from the introducer assembly.

Specifically, with reference to FIG. 3, the jaw opening element 60, has been retracted or pulled back in the proximal direction, by pulling on the wire 64. This causes the enlarged head 62 to contact and then press against the internal surfaces 32, 34 of the pinch points 28, 30 of the detachment mechanism. As a result of the rounded or tapering shape of the enlarged head 62 and the tapering arrangement of the internal surfaces 32, 34, pressure imparted on the enlarged head 62 in the proximal direction, that is against the tapering surfaces 32, 34, will cause the enlarged head to bias the jaw elements 14, 16 apart, in effect opening the detachment mechanism 10. In practice, the jaw elements 14, 16 need be pulled apart only sufficiently to enable the coupling element 76 of the medical device 70 slide out from the distal end of the cup elements 44, 46 of the jaw elements 14, 16.

In this manner, the medical device 70 can be released from the detachment mechanism 10 and in practice from the introducer assembly, as will be described in further detail below. In practice, therefore, the jaw elements 14, 16 will generally be biased apart less than the amount depicted by FIG. 3.

As a result of the resiliency of the detachment mechanism 10 of the preferred embodiment, release of pressure on the jaw opening element 60 will allow the jaw elements 14, 18 to push back by their spring force, towards their at rest and closed positions, as shown in FIGS. 1 and 2. So doing, will urge the enlarged head 62 in a distal direction (forwardly) again into the chamber 48 of the body portion 12. Thus, the detachment mechanism 10 will return to its naturally closed and gripping configuration. This can be used both in retracting the jaw element 10 for removal from within the patient and equally, as will be apparent below, for retrieving an implanted medical device.

Figure 4:
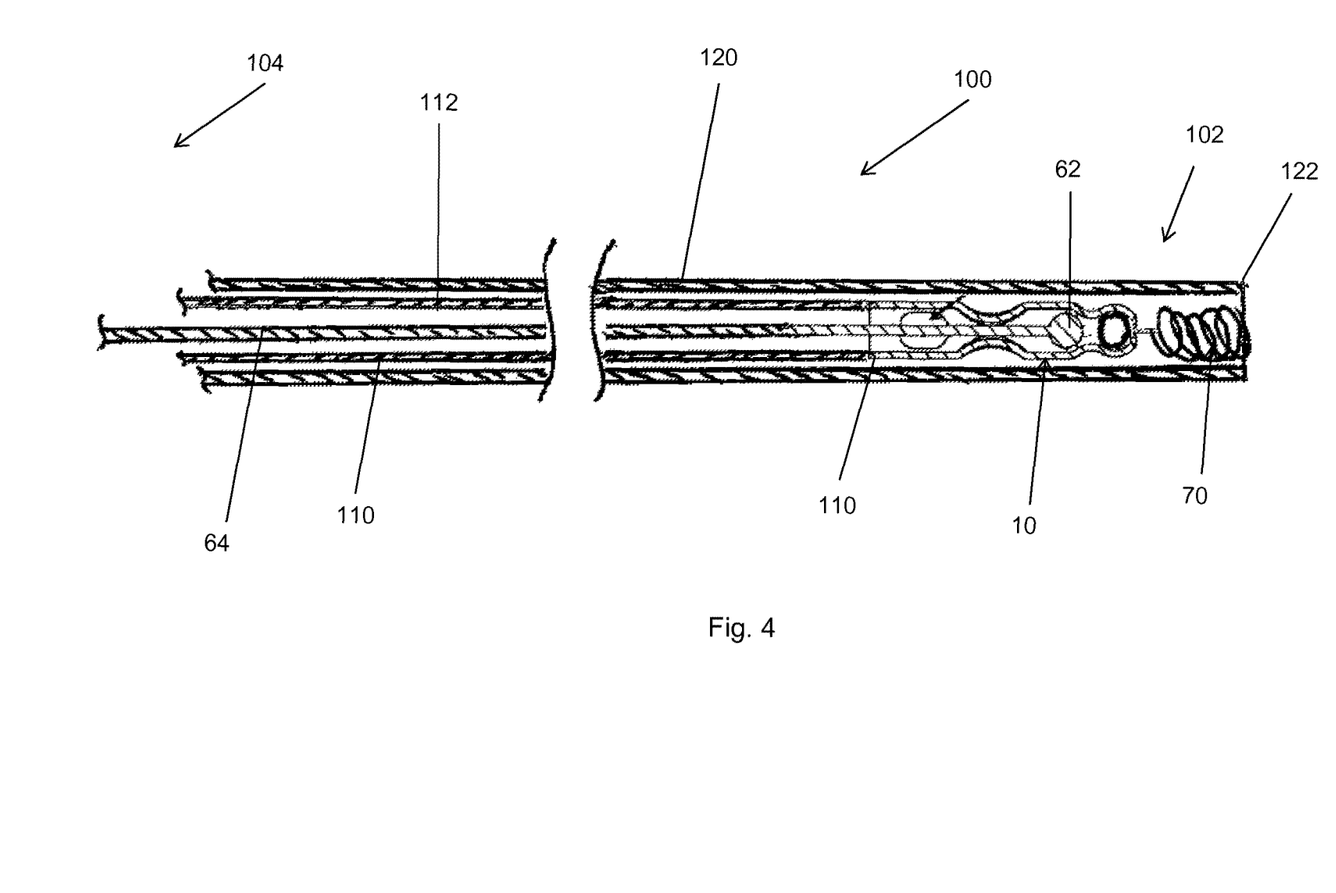
FIG. 4 is a schematic diagram in cross-section of the principal components of an embodiment of introducer assembly including the detachment mechanism of FIGS. 1 to 3.

With reference now to FIG. 4, this shows the major portion of an introducer assembly 100 which has at a distal end 102 the implant detachment mechanism 10, which is disposed and attached to a carrier catheter 110. The carrier catheter 110 is fixed to the proximal end 20 of the body portion 12 of the detachment mechanism 10 in any suitable manner.

The carrier catheter 110 can be of any known structure. It is typically flexible and has sufficient longitudinal strength in order to be pushable through the vasculature of a patient from a remote percutaneous entry point. The carrier catheter 10 includes a lumen 112 in which the wire or rod element 64 can be slidably received.

The introducer assembly 100 also includes an outer sheath 120, which again can be of conventional structure and design. The sheath 120 is typically formed of a resilient polymeric material having one or more strengthening elements embedded therewithin for optimising pushability and kink resistance of the sheath 120. As will be apparent form FIG. 4, the sheath 120 is sized to fit concentrically over the catheter 110, the detachment mechanism 10 and the implantable medical device 70. The sheath 120 is also of a length sufficient to be able to reach to the treatment site within the patient's vasculature while keeping its proximal end to outside the patient. At the proximal end 104 of the introducer assembly 100, there are provided handles/manipulation elements for operating the introducer assembly 100, these being well known in art and therefore not described in further detail or shown in FIG. 4.

As the skilled person will appreciate, once it is suitably positioned in the patient's vasculature, the outer sheath 120 is typically retracted in order to expose the medical device and, in this embodiment, the detachment mechanism 10 in the patient's vessel. Given the fact that the detachment mechanism 10 has a naturally closed configuration, when this is exposed beyond the distal end 122 of the sheath 120, it will remain closed and therefore with the medical device attached thereto. This enables the clinician to adjust the position of the medical device precisely within the vessel before releasing this from the introducer assembly 100. Once the clinician is satisfied that the medical device is properly positioned, the detachment mechanism 10 can be opened, by pulling on the wire 64 whilst simultaneously applying an opposing force to the carrier catheter 110, thereby providing the force required to pull the enlarged head 62 back against the curved surfaces 32, 34 of the gripper arms 14, 16. This force urges the arms to an open position against the spring return force of the body portion 12 of the detachment mechanism 10. At this point, therefore, the implantable medical device 70 can be released from the detachment mechanism 10.

It is also possible, if necessary or appropriate, to retrieve the implantable medical device 70 by means of the detachment mechanism 10, namely by opening the gripper arms 14, 16, placing them around the coupling element 76 of the medical device 70, then releasing, even in controlled manner, the pressure on the gripper arms 14, 16 by releasing the pulling pressure on the wire 64 and hence on the enlarged head 62. This enables the gripper arms 14, 16 to close onto the coupling element 76 such that this becomes firmly grasped by the gripper arms 14, 16. The implantable medical device 70 can then be retracted back into the carrier sheath 120, if necessary, or just repositioned within the patient's vessel.

In the case of embolization coils and similar devices, where the clinician will typically choose which size and/or length of device implant in the course of the procedure, the sheath 120 will typically be positioned within the patient's vasculature first and then the medical device 70 on the carrier catheter 110 fed through the pre-positioned sheath 120. A plurality of medical devices, particularly embolization coils 70, may be deployed in a single procedure, until a desired degree of occlusion has been achieved within the vessel. Prior art carrier devices for embolization coils rely upon the sheath 120 to close the gripper arms, the latter being naturally biased open, and as a result to keep the medical device attached to the introducer assembly. However, different coils require different carrier devices and also suffer from the risk that the coil either will not be properly connected to the carrier assembly 110 or will become detached from it, with the result that it would not be deployed correctly. Moreover, if not properly coupled to the carrier apparatus 110, it will not be possible to pull the medical device backwards in order to reposition it precisely within the vessel.

By contrast, with the apparatus disclosed herein, the detachment mechanism 10 will naturally close in and onto the medical device, with the result that as soon as the medical device is attached to the detachment mechanism 10, the clinician will have confidence that it will remain attached until intentionally detached by operation of the opening element 60, under the clinician's control. In this regard, it is also possible to use a carrier catheter and a medical device which are significantly smaller than the internal dimensions of the carrier sheath 120, without risk of detachment of medical device 70 from the carrier apparatus 110 and thus without risk of incorrect deployment of the medical device, for the reason that the outer sheath 120 does not play any part in holding the gripper arms 14, 16 closed.

As indicated above, the carrier apparatus 110 and sheath 120 can also be used to retrieve a medical device 70 already implanted in a patient's vessel, for instance at the time of first deployment or at the conclusion of a medical treatment. This can be effected in the manner described above.

The stop shoulders 52, 54 prevent the enlarged head 62 from moving forwardly into the chamber 15 where the coupling element 76 of the medical device 70 normally resides. In this regard, it will be apparent that the stop shoulders 52, 54 will be correctly positioned as soon as the enlarged head 62 stops impinging on the curved surfaces 32, 34 whereupon the gripper arms 14, 18 will naturally close again into the configuration shown in FIGS. 1, 2 and 4. In this manner, there is no risk that the jaw opening element 60 will interfere with the coupling 76 of the implantable medical device 70.

The skilled person will appreciate that the enlarged head 62 need not be spherical, as its operative elements are the provision of an enlarged surface which can press upon the tapering surfaces 32, 34. In practice, it is only necessary for one or the other of the surfaces 32/34 and head 62 to be tapering and that therefore in the case of the enlarged head 62 having a tapering proximal surface the surfaces 32, 34 could be non-tapering. It is considered, though, that having rounded tapering surfaces 32, 34 in the body portion 12 and rounded or spherical surfaces to the enlarged head 62, provide optimum functionality.

The skilled person will also appreciate that it is not necessary for the detachment mechanism 10, in particular the body member 12, to be made of a metal or metal alloy, as this can be made of any other resilient material, including polymeric materials. The detachment mechanism 10 could also be made of a plastics material, optionally with one or more resilient strengthening elements integral therewith.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosures in the abstract accompanying this application are incorporated herein by reference.

The invention claimed is:

1. A medical implant detachment device for holding and releasing a medical implant in an introducer assembly, the detachment device having a longitudinal axis, a proximal end and a distal end, and including:

a jaw unit including a plurality of jaw elements located at the distal end of the detachment device, the jaw elements having a closed configuration and an open configuration and being configured to be in the closed configuration when unbiased, the jaw elements forming a medical implant coupling chamber designed to receive a coupling element of a medical implant, the jaw unit including an enclosure separate from the coupling chamber and disposed proximally of the coupling chamber;

a jaw opening element disposed in the enclosure of the jaw unit, the jaw opening element having a first, non-biasing, position maintaining the jaw elements in the closed configuration and being longitudinally movable from the first position to a second position, wherein in the second position the jaw opening element biases the jaw elements from the closed configuration to the open configuration; wherein the jaw opening element includes a head member disposed within the enclosure, wherein the plurality of jaw elements are pinched together at a first pinch point, creating a first portion with radially inward outer walls and radially inward inner walls being rounded along the longitudinal axis or being tapering along the longitudinal axis against which the head member is able to press when longitudinally moved to bias the jaw elements into the open configuration, wherein the plurality of jaw elements are pinched together at a second pinch point, creating a second portion with radially inward outer walls and radially inward inner walls, the second pinch point being distal to the first pinch point and between the enclosure and the coupling chamber along the longitudinal axis, wherein the inner walls and the outer walls of the second pinch point open radially outward towards the coupling chamber.

2. The device according to claim 1, wherein the second position of the jaw opening element is proximal of the first position, and the jaw opening element is retracted proximally in the longitudinal direction to open the jaw elements.

3. The device according to claim 1, wherein the head member is rounded or spherical.

4. The device according to claim 1, including an end-stop adjacent the jaw elements.

5. The device according to claim 4, wherein the end stop is disposed in the enclosure.

6. The device according to claim 1, including a trigger wire having a proximal end and a distal end, the distal end of the trigger wire being attached to the jaw opening element and the proximal end of the trigger wire being actuatable to retract the jaw opening element proximally in the longitudinal direction from the first position to the second position.

7. The device according to claim 1, wherein the jaw elements have facing concave inner surfaces.

8. The device according to claim 7, wherein the concave inner surfaces of the jaw elements are partially spherical.

9. The device according to claim 1, including two jaw elements, disposed substantially opposite one another.

10. The device according to claim 1, wherein the detachment device is formed from a cannula, the jaw elements being cut from the cannula.

11. An introducer assembly including:
a medical implant detachment device according to claim 1;
a catheter having a proximal end and a distal end, the distal end being coupled to the detachment device;
an outer sheath within which the catheter and detachment device are locatable; and
an implantable medical device having a coupling element disposed within the chamber of the jaw elements of the detachment device, the coupling element being held in the chamber by the closed configuration of the jaw elements.

12. The introducer assembly according to claim 11, wherein the medical device is an embolization coil.

* * * * *